United States Patent
Co et al.

(10) Patent No.: US 11,600,362 B2
(45) Date of Patent: Mar. 7, 2023

(54) VISUALLY REPRESENTING CONCEPTS AND RELATIONSHIPS ON AN ELECTRONIC INTERFACE FOR DELIVERED CONTENT

(71) Applicant: International Business Machines Corporation, Armonk, NY (US)

(72) Inventors: Hau Co, Sharon (CA); Jane Depgen, Boston, MA (US); Joseph Lam, Markham (CA); Vincent Charles Snagg, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 276 days.

(21) Appl. No.: 17/039,284

(22) Filed: Sep. 30, 2020

(65) Prior Publication Data

US 2022/0101950 A1     Mar. 31, 2022

(51) Int. Cl.
    *G06F 3/048*      (2013.01)
    *G16B 45/00*      (2019.01)
    *G06F 40/103*      (2020.01)
    *G16H 50/20*      (2018.01)

(52) U.S. Cl.
    CPC ........... *G16B 45/00* (2019.02); *G06F 40/103* (2020.01); *G16H 50/20* (2018.01)

(58) Field of Classification Search
None
See application file for complete search history.

(56) References Cited

U.S. PATENT DOCUMENTS

| | | | |
|---|---|---|---|
| 6,629,097 B1 | 9/2003 | Keith | |
| 7,219,307 B2 | 5/2007 | Senay | |
| 7,379,880 B1 | 5/2008 | Pathria | |
| 7,831,827 B2 | 11/2010 | Walmsley | |

(Continued)

OTHER PUBLICATIONS

"Accessible Color Palette Evaluator", NC State University IT Accessibility Resources, Last printed Sep. 29, 2020, 2 pages, <https://accessibility.oit.ncsu.edu/tools/color-contrast/index.php?colors=0098ff>.

(Continued)

*Primary Examiner* — William C Trapanese
(74) *Attorney, Agent, or Firm* — Michael A. Petrocelli

(57) ABSTRACT

A computer distinguishes relationships among concepts of conveyance contained within delivered content. The computer receives several of concepts of conveyance and determines a first visual identification indicia for a first of the concepts, with the first visual identification indicia being characterized by a first combination of appearance style elements selected from a group of visual attribute categories. The appearance style elements have sufficient visual contrast relative to one another to represent distinguishable relationships among individual concepts of conveyance, pairs of concepts of conveyance and multiple concepts of conveyance that are overlapping. The computer iteratively determines a visual identification indicia for each concepts of conveyance. The visual identification indicia are characterized by a unique corresponding combination of appearance style elements selected from the visual attribute categories. The computer presents a visualization of concepts of conveyance in a manner that distinguishes relationships among the concepts of conveyance.

20 Claims, 8 Drawing Sheets

(56) References Cited

U.S. PATENT DOCUMENTS

| | | | |
|---|---|---|---|
| 9,064,008 B2 | 6/2015 | Knight | |
| 2009/0327883 A1* | 12/2009 | Robertson | G06F 16/44 707/999.102 |
| 2014/0101006 A1 | 4/2014 | Pitt | |
| 2018/0067998 A1* | 3/2018 | Sherman | G06F 16/248 |

OTHER PUBLICATIONS

"Accessible multi-category visible cross references", An IP.com Prior Art Database Technical Disclosure, Disclosed Anonymously, IP.com No. IPCOM000239036D, IP.com Electronic Publication Date: Oct. 2, 2014, 4 pages, <https://priorart.ip.com/IPCOM/000239036>.

"ADA Website Compliance Lawsuits: Recent and High-Profile", Lovata blog, Mar. 5, 2018, 33 pages, <https://lovata.com/blog/ada-website-compliance-lawsuits-recent-and-high-profile.html>.

"Shape Tool", © 2020 National Council of Teachers of Mathematics, 3 pages, <https://www.nctm.org/Classroom-Resources/Illuminations/Interactives/Shape-Tool/>.

"The Business Case for Digital Accessibility", Web Accessibility Initiative (WAI), W3C, Published Nov. 9, 2018, 13 pages, <https://www.w3.org/WAI/business-case/>.

"The Visual Language of Dashed Lines", Brainy Stuff, Last printed Mar. 7, 2020, 7 pages, <http://understandinggraphics.com/brainy/the-visual-language-of-dashed-lines/>.

Higgins, Tucker, "Supreme Court hands victory to blind man who sued Domino's over site accessibility", CNBC, Published Mon, Oct. 7, 2019, 3 pages, <https://www.cnbc.com/2019/10/07/dominos-supreme-court.html>.

Mell et al., "The NIST Definition of Cloud Computing", National Institute of Standards and Technology, Special Publication 800-145, Sep. 2011, 7 pages.

Patton, Carol, "Lawsuits Soar over Inaccessible Websites", National Organization on Disability, Sep. 5, 2018, 6 pages, <https://www.nod.org/lawsuits-soar-over-inaccessible-websites/>.

Rosebrock, Adrian, "OpenCV shape detection", PyImageSearch, Feb. 8, 2016, 7 pages, <https://www.pyimagesearch.com/2016/02/08/opencv-shape-detection/>.

Vu, et al., "2017 Website Accessibility Lawsuit Recap: A Tough Year for Businesses", ADA Title III, Jan. 2, 2018, 3 pages, <https://www.adatitleiii.com/2018/01/2017-website-accessibility-lawsuit-recap-a-tough-year-for-businesses/>.

* cited by examiner

VISUALLY REPRESENTING CONCEPTS AND RELATIONSHIPS ON AN ELECTRONIC INTERFACE FOR DELIVERED CONTENT

BACKGROUND

The present invention relates generally to the field of visually representing diagnostic concepts in computer generated output, and more specifically, to computerized user interface systems that portray relationships among conveyed concepts in a discernable and visually-accessible manner.

Computer generated output can be used to accomplish a wide variety of tasks. Diagnostic content, for example, may contain information useful when determining appropriate courses of action for assessed conditions. Computer augmentation can make diagnostic output especially useful by showing relationships among complex topics that may be otherwise difficult to discern. Computerized user interfaces may indicate patterns and interrelated concepts that can allow for sophisticated diagnosis and specialized treatment.

SUMMARY

According to one embodiment, a computer-implemented method to distinguish relationships among concepts of conveyance contained within delivered content includes receiving, by the computer, a group of concepts of conveyance. The computer determines a first visual identification indicia for the first concept, with the first visual identification indicia being characterized by a first combination of appearance style elements selected from a group of visual attribute categories. The appearance style elements have sufficient visual contrast relative to one another to represent distinguishable relationships among individual concepts of conveyance, pairs of concepts of conveyance and multiple concepts of conveyance that are overlapping. The computer iteratively determines a visual identification indicia for each of the concepts of conveyance, and each visual identification indicia is characterized by a unique combination of appearance style elements selected from visual attribute categories. The computer presents a visualization of the concepts of conveyance, with the visualization distinguishing relationships among the concepts of conveyance. According to aspects of the invention, the appearance style elements are selected, at least in part, in accordance with visual accessibility consideration factors. According to aspects of the invention, the visual identification indicia are line segments; and the appearance style elements are selected from a list consisting of indicia endmarks, indicia line style, indicia line thickness, and indicia line color. According to aspects of the invention, one of the selected appearance style elements includes a first indicia endmark and a second indicia endmark, and first and second endmarks are different. According to aspects of the invention, the selected appearance style elements include a plurality of line styles. According to aspects of the invention, one of the selected appearance style elements includes a plurality of line thicknesses. According to aspects of the invention, the visual identification indicia have at least one attribute in common. According to aspects of the invention, at least two of the concepts of conveyance share a common characteristic and the visual identification indicia are selected, at least in part, in accordance with the shared characteristic.

According to another embodiment, a system to optimize input component enablement to distinguish relationships among concepts of conveyance contained within delivered content, which comprises: a computer system comprising a computer readable storage medium having program instructions embodied therewith, the program instructions executable by a computer to cause the computer to: receive a plurality of concepts of conveyance; responsive to receiving said plurality of concepts of conveyance, determine a first visual identification indicia for a first of said plurality of concepts of conveyance, said first visual identification indicia being characterized by a first combination of appearance style elements selected from a plurality of visual attribute categories, wherein said appearance style elements have sufficient visual contrast relative to one another to represent distinguishable relationships among individual concepts of conveyance, pairs of concepts of conveyance and multiple concepts of conveyance that are overlapping; responsive to determining said first visual identification indicia, iteratively determine a corresponding visual identification indicia for each of said remaining plurality of concepts of conveyance, each of said visual identification indicia being characterized by a unique corresponding combination of appearance style elements selected from said plurality of visual attribute categories; responsive to determining said visual identification indicia for each concept of conveyance, present a visualization of said plurality of concepts of conveyance, said visualization distinguishing relationships among said plurality of concepts of conveyance.

According to another embodiment, a computer program product to distinguish relationships among concepts of conveyance contained within delivered content, the computer program product comprising a computer readable storage medium having program instructions embodied therewith, the program instructions executable by a computer to cause the computer to: receive, using said computer, a plurality of concepts of conveyance; responsive to receiving said plurality of concepts of conveyance, determine, using said computer, a first visual identification indicia for a first of said plurality of concepts of conveyance, said first visual identification indicia being characterized by a first combination of appearance style elements selected from a plurality of visual attribute categories, wherein said appearance style elements have sufficient visual contrast relative to one another to represent distinguishable relationships among individual concepts of conveyance, pairs of concepts of conveyance and multiple concepts of conveyance that are overlapping; responsive to determining said first visual identification indicia, iteratively determine, using said computer, a corresponding visual identification indicia for each of said remaining plurality of concepts of conveyance, each of said visual identification indicia being characterized by a unique corresponding combination of appearance style elements selected from said plurality of visual attribute categories; responsive to determining said visual identification indicia for each concept of conveyance, present, using said computer, a visualization of said plurality of concepts of conveyance, said visualization distinguishing relationships among said plurality of concepts of conveyance.

The present disclosure recognizes the shortcomings and problems associated with processing assessment documents. Aspects of the embodiment generate processed assessment documents (including, for example, situational descriptions, conditional reports, professional diagnoses in a variety of fields, and other similar content) that visually identify distinct concepts of conveyance (COCs) and relationships among the COCs (including, for example, diagnostic themes) in a clear manner. According to aspects of the invention, the processed assessment documents will improve the usefulness of the document as a diagnostic tool, by ensuring that complex concept data is communicated clearly and accessible to a wide audience. Aspects of this invention graphically identify relationships among individual concepts, pairs of concepts and multiple concepts that are overlapping with the use of rule decoration, symbols, shapes and/or patterns, and color and without the need to use background colors. Other aspects of the invention make identifying relationships in processed versions of delivered content easier, allowing a recipient of the processed content to connect concepts quickly at a glance. As used herein, the term "visually-accessible" means useable in a functional manner for audience members who have limited sight capacity (e.g., people who are visually impaired, people who have color blindness, and people who use assistive reading technologies, including legally blind audience members). The term is used to indicate readiness for access by screen readers and other assistive technology that may help identify and interpret content for audience members who need or desire such assistance.

In embodiments according to the present invention, a computer implemented method to optimize input component enablement for several participants in an electronic group meeting includes a computer that identifies a group of communication devices (e.g., computers, telephones, etc.) joined together for use by a group of meeting participants. Each of the communication devices has a microphone, each of the participants is associated with one of the microphones, and some of the participants are characterized by identification attributes (for example, participant name or subject matter expertise). The computer receives audio input from the participants via the microphones and measures certain quality-based attributes of the audio input to provide associated quality metrics. The audio input can include any audio throughput received by the computer, which can include background noise, a participant's voice, and meeting content, as well as audio signal quality assessments. The computer uses these metrics to determine whether any of the input exceeds a quality threshold and places microphones providing quality threshold-exceeding input into an active speaking mode. The computer also evaluates content of participant audio input and identifies a current concept of focus. The computer then places into an active speaking mode any microphones that are associated with participant having identification attributes that correspond to the current concept of focus.

In another embodiment of the invention, a system to optimize input component enablement for a plurality of communication devices each having an input component associated with at least one participant in an electronic group meeting, which comprises:

a computer system comprising a computer readable storage medium having program instructions embodied therewith. The program instructions are executable by a computer to cause the computer to: identify a plurality of communication devices, each having an audio input component, said audio input components each being associated with at least one of a plurality of a group of participants, wherein at least one of said participants is characterized by an identification attribute; receive an audio input from a first of said audio input components; measure preselected qualitative attributes of said audio input to provide a set of quality metrics; determine whether said set of quality metrics exceeds a threshold for quality; place into an active speaking mode said first audio input component when said set of quality metrics exceeds said threshold for quality; evaluate content of said audio input to identify a concept of focus; place into an active speaking mode any audio input component associated with one of said participants characterized by said identification attribute when said identification attribute corresponds to said identified concept of focus.

In another embodiment of the invention, a computer program product optimizes input component enablement for a plurality of participants in an electronic group meeting. The computer program product comprises a computer readable storage medium having program instructions embodied therewith. The program instructions are executable by a computer to cause the computer to: identify a plurality of communication devices, each having an audio input component, said audio input components each being associated with at least one of a plurality of group participants, wherein at least one of said participants is characterized by an identification attribute; receive an audio input from one of said audio input components; measure content and preselected qualitative attributes of said audio input to provide, respectively, a topic of focus and a set of quality metrics; determine whether said set of quality metrics exceeds a threshold for quality; and place into an active speaking mode any audio input component that is associated with one of said participants having an identification attribute corresponding to said topic of focus or for which said set of quality metrics exceeds said threshold for quality.

Assessment documents can be processed to visually identify individual concepts and to highlight relationships among them. Such processing can make a given assessment document more useful. For example, processing to provide visual indicia showing how concepts are connected can improve diagnosis accuracy and overall assessment efficacy. Processing a document to include visual indications of overlapping concepts can also improve diagnosis speed and make treatment plan generation more efficient. It is important when processing assessment documents to present distinct concepts and information about concept relationships to include consider presentation approaches that are effective for a broad audience.

Assessment documents (e.g., such as situational descriptions, conditional reports, professional diagnoses, and other similar delivered content) often contain detailed information with complex meanings. The information can include interrelated concepts, and many times, even concepts that are presented individually throughout a given document are connected in ways that, if properly presented, can reveal complex themes.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. The drawings are set forth as below as.

DETAILED DESCRIPTION

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a participant" includes reference to one or more of such participants unless the context clearly dictates otherwise.

Figure 1:
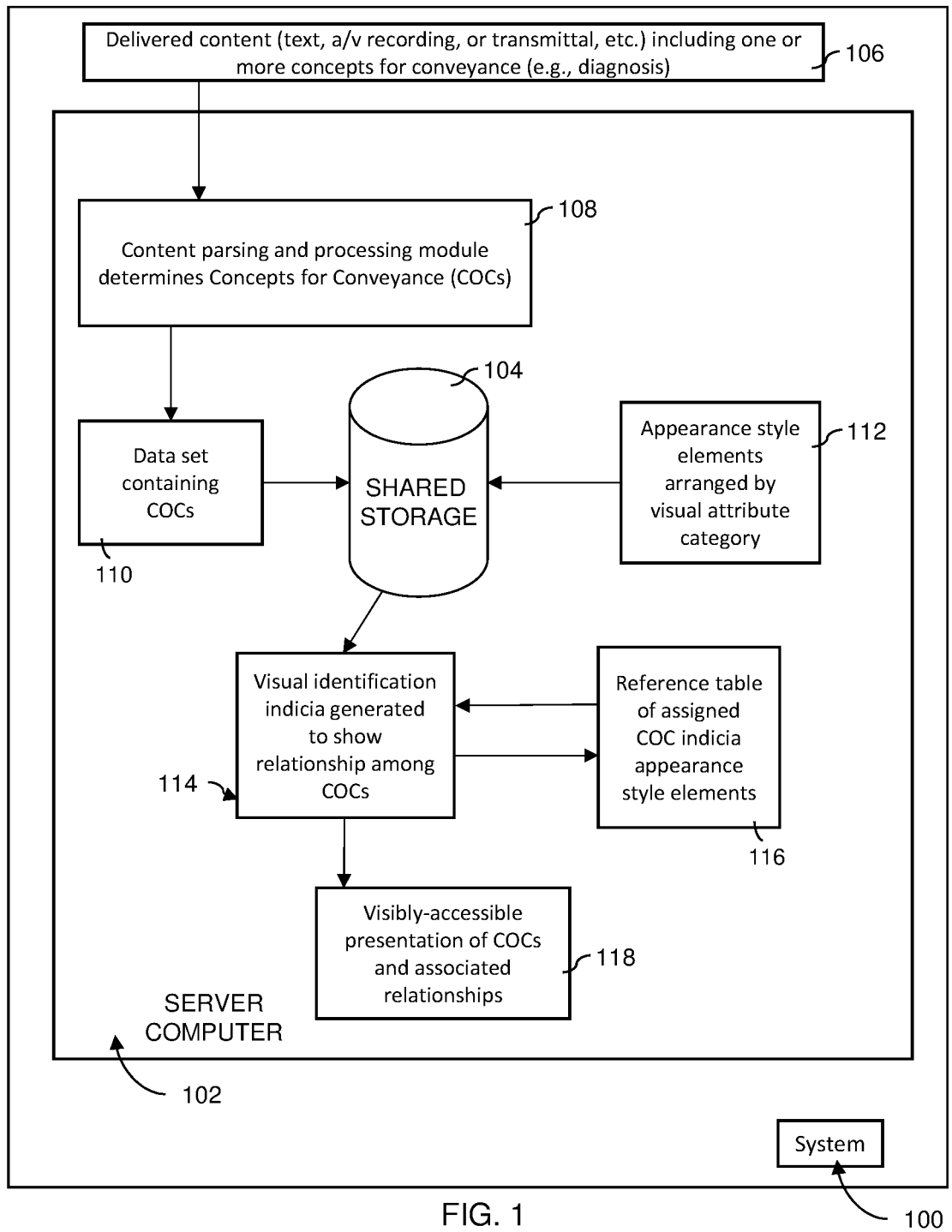
FIG. 1 is a schematic block diagram illustrating an overview of a system for computer-implemented processing of assessment documents to identify distinct concepts of conveyance and relationships among them in a clear and visually-accessible manner.
Figure 2:
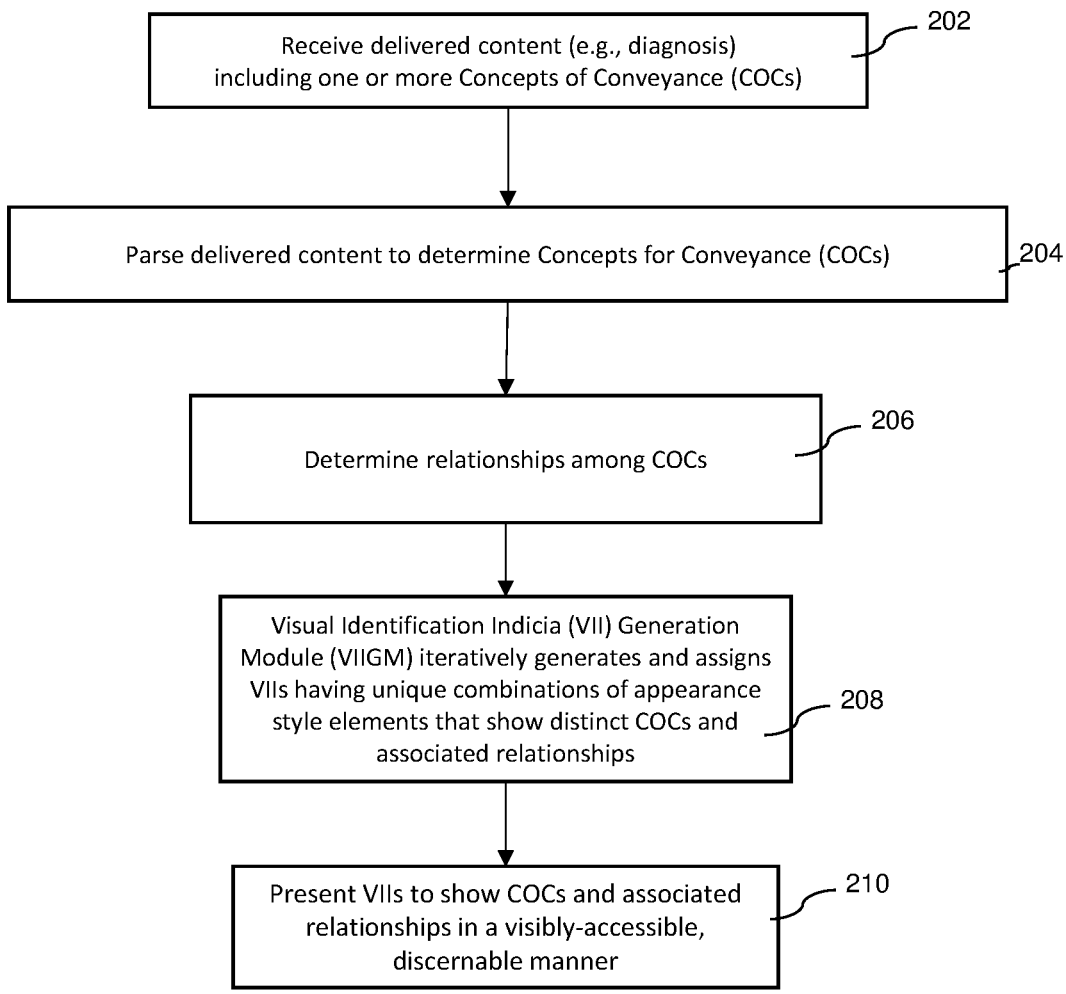
FIG. 2 is a flowchart illustrating a method, implemented using the system shown in FIG. 1, of processing of assessment documents to identify distinct concepts of conveyance and relationships among them in a clear and visually-accessible manner, according to aspects of the invention.

Now with combined reference to the Figures generally and with particular reference to FIG. 1 and FIG. 2, an overview of system 100 in which a method 200 for computer-implemented processing of delivered content 106 (such as a medical diagnosis or other similar assessment document) may be applied is shown. According to aspects of the invention, the method identifies distinct concepts of conveyance (COCs) 110 in the delivered content 106, as well as relationships among the COCs. The method 200 is usable within a system 100 carried out by a server computer 102 having optionally shared storage 104 and aspects that portray the COCs 110 and relationships in a clear and visually-accessible manner.

The server computer 102 receives delivered content 106 (e.g., an assessment document, such as a medical diagnosis, a situational assessment, a conditional description, a professional analysis, and the like), and the content is passed along to a Content Parsing and Processing Module (CPPM) 108, where the content 106 is parsed and COCs 110 contained in the content are identified. The server computer 102 collects the COCs 110 generated by the CPPM 108 into a COC data set, for further processing. Although delivered content 106 is described herein as including assessment documents, it is noted that the delivered content 106 need not be limited to documents and could arrive in many formats (e.g., including text, audio, and video recordings, lab notes and reports of various type, etc.).

Figure 5:
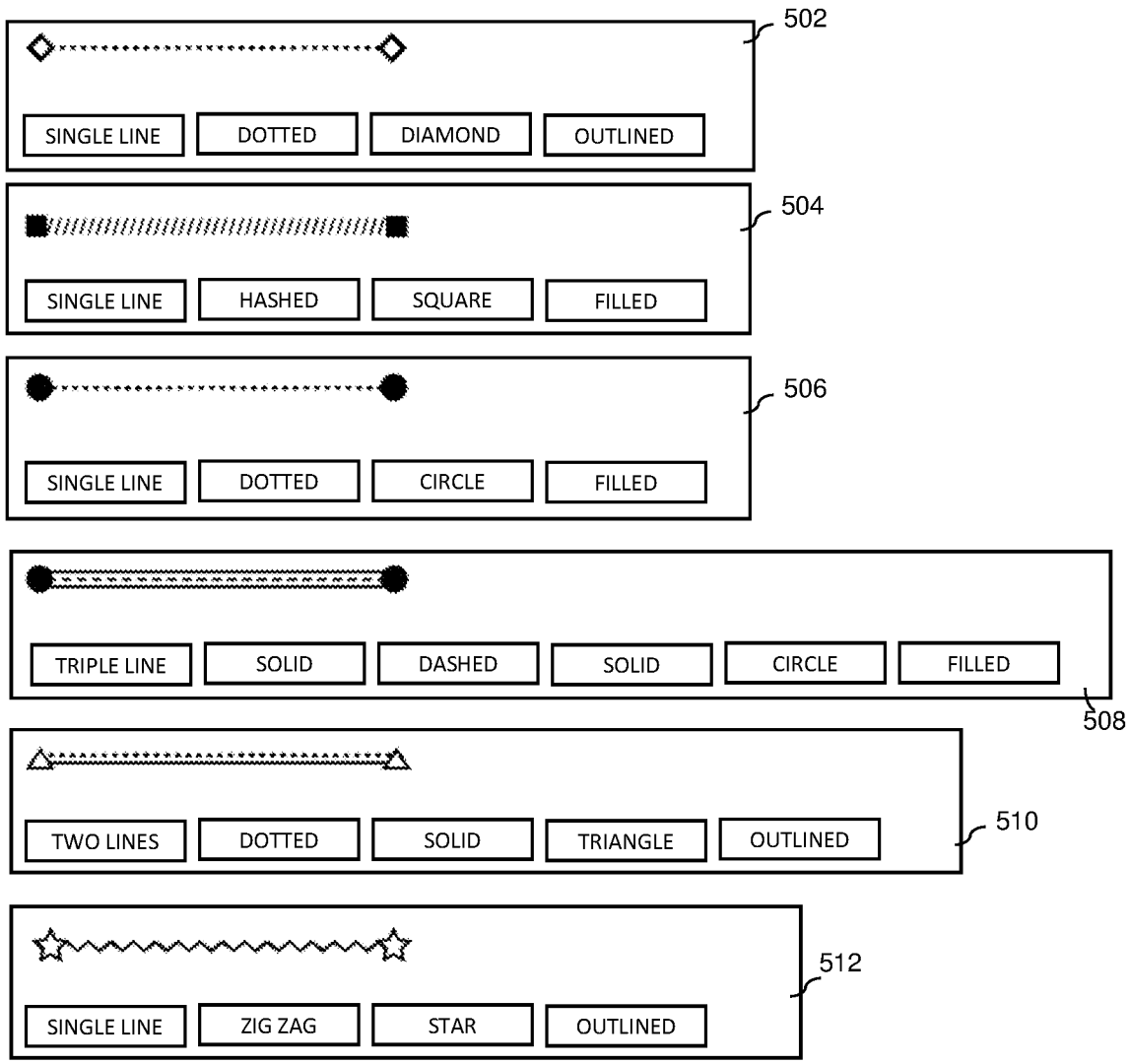
FIG. 5 is a collection of visual identification indicia for concepts of conveyance generated in accordance with aspects of the invention flowchart illustrating aspects of a Visual Identification Indicia Generation Module used in the method, implemented using the system shown in FIG. 1, of processing of assessment documents to identify distinct concepts of conveyance and relationships among them in a clear and visually-accessible manner, according to aspects of the invention.

The ASEs 112 are used to define Visual Identification Indicia (VIIs) 114 for each of the identified COCs 110. Examples of VIIs are shown in FIG. 5 and will be discussed more fully below. Each VII 112 is characterized by a unique set of ASEs 112, with certain (but not entire sets of) ASEs possibly being repeated and used in to show relationships among related COCs 110. Partial reuse of ASEs allows aspects of the present invention to clearly identify which COCs are related or otherwise have attributes in common.

To ensure that each of the VIIs 114 includes ASEs that accurately portray whether a given COC 110 is related to other COCs, the server computer 102 stores the ASEs assigned to each COC in a reference table 116. The server computer 102 indexes the reference table 116 by COC and uses the table contents when generating the VIIs 114.

When each COC 110 has been assigned a distinct VII, the server computer 102 presents a processed version 118 of the delivered content 106. According to aspects of the present invention, the processed version 118 of the delivered content 106 shows each distinct COC 110, as well as associated relationships between and among the COCs in a visually-accessible manner. These relationships are shown in particular through the use of line segments with different appearance qualities, including line styles and thicknesses (e.g., including variations of single line thickness and quantities of lines stacked or bundled) and through the use of distinctive endmarks. As used herein, the term "endmark" means various endpoints, endmarks, point symbols, shapes, patterns, and other indicia selected by one skilled in this field (e.g., including colors chosen as visually-distinct without the need to use background colors) to indicate line segment termination).

Now with continued reference to FIG. 1, and with particular reference to FIG. 2, the method 200 of processing delivered content and portraying relationships among conveyed concepts 110 in a discernable and visually-accessible manner according to the present invention is discussed in further detail. The server computer 102 receives delivered content 106, such as an assessment document (e.g., a medical diagnosis, situational description, conditional report, professional assessment, etc.), at block 202.

According to aspects of the invention, delivered content 106 often includes mixtures of various kinds of information, some of which is easy to understand and some of which is more complex. Within this mix, the delivered content typically includes multiple COCs 110, that may each stand alone, or which may belong to a group of overlapping, or otherwise related COCs. In a medical setting, typical COCs 110 include body parts or organs affected, illness classification, clinical attributes, general patient findings, temporal concepts, spatial concepts, and qualitative concepts, and other diagnostic themes known to and used by medical professionals to assess patient condition and to recommend treatment. In general, according to aspects of the present invention, the audience for the delivered content 106 may rely on the content 106 to make recommendations or other informed decisions, and having the COCs and associated relationships presented effectively makes the content easier to use and provides more-accurate decisions.

To ensure clear presentation of the information contained in the delivered content 106, the server computer 102 parses, at block 204, the delivered content to identify individual COCs 110 and, in block 206, determines whether and how the COCs are related. This parsing (and subsequent relationship identification) is preferably done through known artificial intelligence (AI) techniques, such as sentiment analysis, aspect mining, topic modeling, or other typical natural language processing (NLP) approaches. Other suitable approaches may be selected in accordance with the judgment of one skilled in field.

The server computer 102, in a Visual Identification Indicia Generation Module (VIIGM) 208, iteratively generates and assigns a unique VII 114 for each COC 108. As will be described more fully below, the VIIs 114 each have a unique combinations of ASEs 112 that, when presented as a group, show distinct COCs 110, as well as associated relationships among and between them. According to aspects of the invention, the VIIGM 208 uses the reference table 116, aspects of entries for which are shown at FIG. 5, to ensure individual concepts 110 and associated relationships identified in blocks 204 and 206 are represented in a clear and visually-accessible manner to help the information contained in the delivered content 106 reach a broad audience.

The server computer 102 presents at block 210, after iteratively assigning unique VIIs 114 to each COC 110 in the VIIGM 208, a modified version of the delivered content 106 that has been processed to clearly show each COC 110 and associated relationships. According to aspects of the invention, this presentation 210 delivers processed content 106 using unique combinations of ASEs that are visually accessible and easily discernable. This allows the present invention to effectively and efficiently present individual the concepts 110 and complex themes contained within overlapping and otherwise-related concepts in processed assessment documents and other delivered content 106 to a broad audience.

Now with continued reference to FIG. 2 and with additional reference to FIG. 3 and FIG. 4, ASE selection and VII generation using the VIIGM 208 of the present invention will be described in more detail. The VIIGM 208 generates a unique VII for each COC 110, and the server computer 102 will, using information from the COC-indexed reference table 116, share ASEs across COCs to show when COCs are related. Since each VII is characterized by multiple style elements 112, the VIIs are complex, yet distinct and easy to identify.

Figure 3:
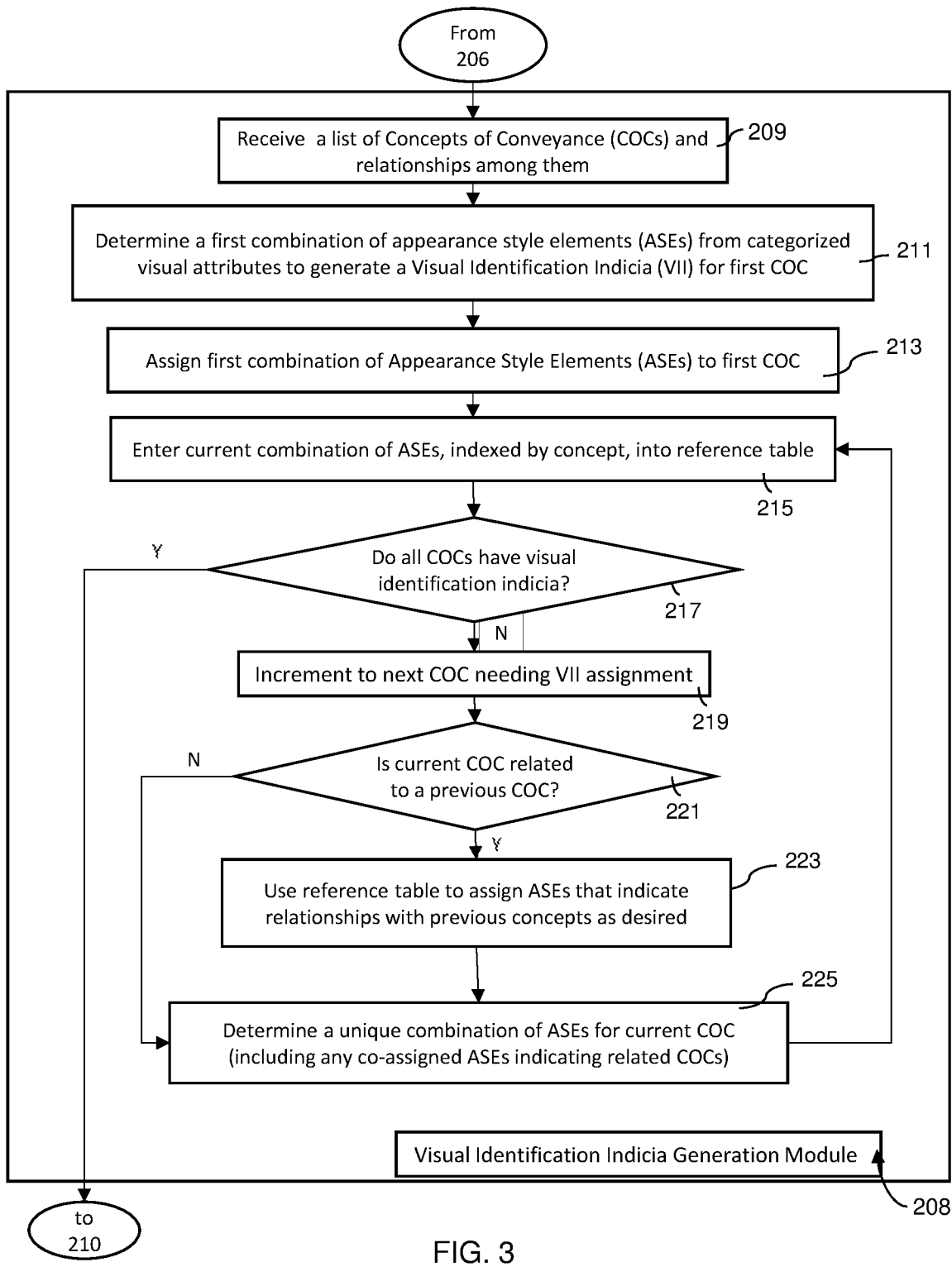
FIG. 3 is a flowchart illustrating aspects of a Visual Identification Indicia Generation Module used in the method, implemented using the system shown in FIG. 1, of processing of assessment documents to identify distinct concepts of conveyance and relationships among them in a clear and visually-accessible manner, according to aspects of the invention.
Figure 4:
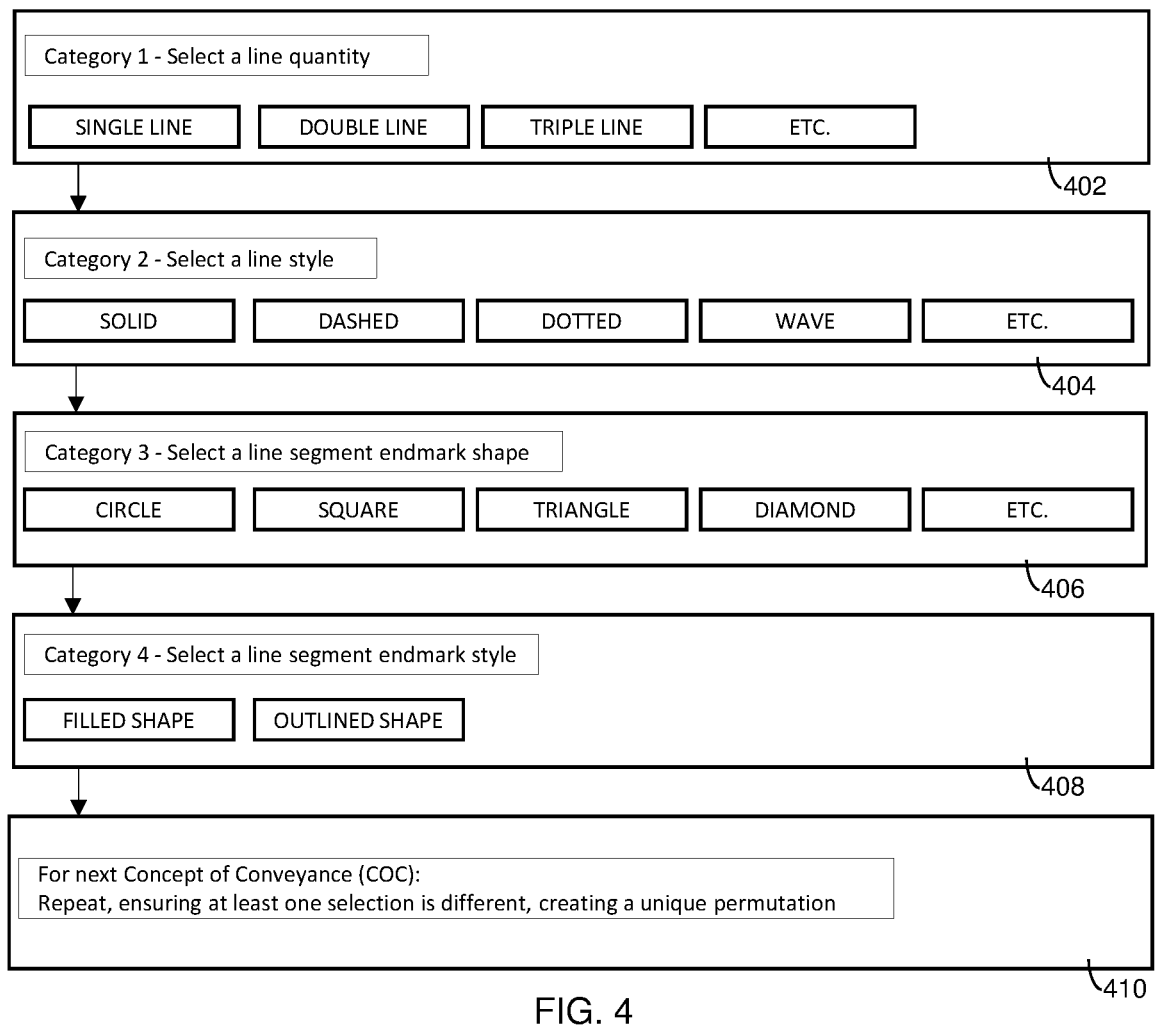
FIG. 4 is a collection of style element categories used in determining visual identification indicia for concepts of conveyance, according to aspects of the invention.

A schematic overview of the selection process conducted by the server computer 102 in the VIIGM 208 is shown with additional reference to FIG. 3 and FIG. 4. In particular, FIG. 4 shows, at a conceptual level that the server computer 102 selects a unique combination of ASEs 112 for each COC. The server computer 102, for example selects a line segment quantity or thickness (e.g., single, double stack, triple stack, etc.) at block 402, with the line quantity being selected (and possibly repeated) to correctly represent related concepts 110 if appropriate and desired. The line quantity 402 selected for VIIs 114 can vary from a single line, to double line, triple line, and so on. Next, the server computer 102 selects a line style (e.g., solid, dashed, dotted, wave, zig zag, etc.) is selected at block 404, with the line style chosen (and possibly repeated) to correctly represent related concepts if appropriate and desired. The server computer 102 selects an endmark shape (e.g., circle, square, triangle, diamond, etc.) at block 406, with the endmark shape being selected (and possibly repeated) to correctly represent related concepts if appropriate and desired. At block 408, the server computer 102 selects an endmark style (e.g., hollow, filled, etc.) at block 408, with the endmark style being selected (and possibly repeated) to correctly represent related concepts if appropriate and desired.

According to one embodiment, VIIs 114 are generated by selecting one ASE 112 from each of four categories, including line quality 402, line style 404, endmark shape 406, and endmark style 408. Although these four style element categories are preferred, ASEs 112 may be selected from other categories in accordance with the judgement of one skilled in this field. Conceptually, the server computer selects one full set of ASEs 112 for each COC 110, iteratively looping from block 402 through to block 410 to until each COC is assigned a unique VII 114. For each iteration, the server computer 102 preferably moves from top to bottom (e.g., blocks 402, 404, 406, and 408) and from left to right among the options available for each ASE 112 when generating VIIs, but other selection arrangements can be selected by one skilled in this field. It is also noted that in addition to line quantity options shown in block 402, line thickness for a single line segment can also be selected as an ASE 112 for heightened visual impact. Additionally, broken lines of the type represented in block 404 may be shown with a variety of line and space proportions, with line and space being equally proportioned or with either line or space being larger than the other to provide line segment variety and heightened visual impact.

The VII generation flow logic will now be discussed in detail, with particular reference to FIG. 3. The server computer 102 receives, at block 209, a data set listing each of the COCs 110 contained in delivered content 106. The server computer 102 determines, at block 211, a first combination of ASEs 112 (as shown in FIG. 4 and discussed above) for the first COC identified in the COC data set 110. The server computer 102 assigns the first ASEs 112 to the first COC at block 213. The server computer records, at block 215, the current combination of ASEs 112 is recorded in the reference table as a COC-indexed entry for use in generating additional VIIs. Since, according to aspects of the invention, generation of VIIs 114 is preferably iterative, the server computer 102 consults the reference table 116, at block 217, to determine whether all identified COCs 110 have been assigned VIIs. If COCs in the data set 110 still need VIIs, the server computer 102 iterates, at block 219, to the next concept in the COC data set.

The server computer 102, at block 221, consults information received in block 209 to determine whether the now-current COC 110 is related to a previous COC. If the current COC 110 is related to a previous COC (or multiple COCs), the server computer 102 will use reference table 116 to assign ASEs 112 that indicate the current COC is related to other COCs. For example, if the current COC is related to a COC with a VII 208 characterized by circular endmarks (as shown in block 506), the current COC may also be assigned the circular endmark ASE. If, for example, the current COC 110 is also related to another COC characterized by a dotted line segment style (as shown in block 502), the current COC may be assigned the dotted line segment style, as well. According to aspects of the invention, several ASEs may be used more than once (e.g., line segment quantity or thickness, endmark shape, or line quality may be repeatedly selected and associated with several COCs 110), and such ASE reuse is preferably done to show related concepts. It is noted, however, that ASE re-use may be merely for the sake of simplicity, if showing relationships among concepts is not of importance to the intended audience. It is noted that if the intended audience for particular kind of delivered content is only interested in having COCs 110 identified, without additional information about COC relationships, the coordinated reuse of ASEs 112 described above is not required.

The server computer 102 collects, at block 225, determines a unique set of ASEs 112 for the current COC, with the ASE set including any ASEs identified for strategic reuse in block 223 if the current COC is related to previous COCs and indication of such relationship is desired. If no ASE reuse is appropriate or desired, a unique full set of ASEs is determined for the current COC, and a VII characterized by the current set of ASEs 112 is assigned to the current COC. The server computer 102 logic flow returns to block 215, where the current set of ASEs 112 is entered in the reference table as a COC-indexed entry. The server computer 102 then returns to block 217 to iteration generate a VII 114 for the next COC 110, unless all COCs in the data set have been assigned a VII. Once VIIs 114 have been assigned to all COCs in the data set 110, logic flow leaves the VIIGM 208 and moves to block 210, where the server computer 102 present the processed version of the delivered content 106, including the VIIs generated for each COC.

With particular reference to FIG. 5, examples of various VIIs 114 for COCs 110 are shown. For example, a first VII 502 having a single dotted line segment, with hollow, diamond endmarks is shown. A second VII 504 is shown with a single hashed line segment having filled, square endmarks. A third VII 506 is shown with a single dotted line segment, with solid, round endmarks is shown. A fourth VII 508 is shown with a dashed/solid/dashed, triple-thickness line segment, having solid, round endmarks. A fifth VII 510 is shown with a dotted/solid, double-thickness line segment, having hollow, triangle-shaped endmarks. A sixth VII 512 is shown, with a single zig zag line segment having hollow, star-shaped endmarks. Other and additional combinations a possible, and the server computer 102 records the ASEs for each COC allow in the reference table to ensure that unique permutations are generated to identify distinct COCs and that style elements can be shared where needed to show relationships among concepts.

Figure 6:
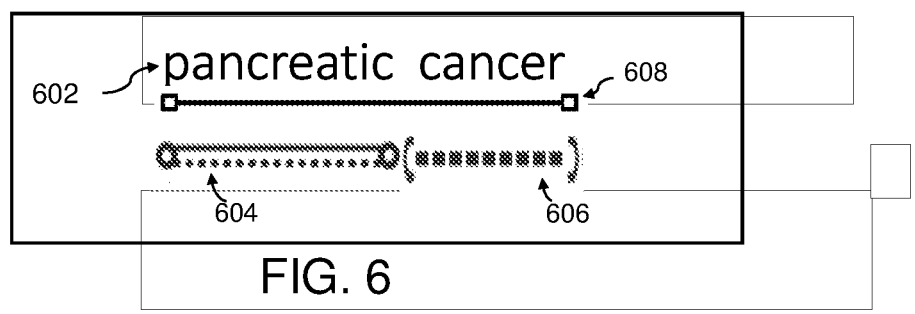
FIG. 6 is an example of modified delivery content processed to identify distinct concepts of conveyance and relationships among them in a clear and visually-accessible manner, according to aspects of the invention.

With reference to FIG. 6, a modified (e.g., parsed and processed) portion of delivered content 106 that includes the phrase "pancreatic cancer" 602 is shown. Once parsed and processed, the phrase is shown to include two distinct concepts of conveyance, "pancreatic" and "cancer", as well as the compound or overlapping concept, "pancreatic cancer" formed from these two complementary concepts. The VIIGM 208 of the server computer 102 has generated three VIIs for COCs identified at block 204 as COCs. In particular, the VIIGM has generated VIIs for the distinct concepts "pancreatic" 604 and "cancer" 606, as well as for the compound concept "pancreatic cancer" 608, and the VIIs for these concepts are shown graphically in FIG. 6. The pancreatic VII 604 is characterized by a double line quantity style element 402. The pancreatic VII 604 is further characterized by a line style element 404, with one solid line segment and one dashed-style line segment. The pancreatic VII 604 is further characterized by endmark shapes 406 that are rounded. The pancreatic VII 604 is further characterized by endmark style element 406 of outlined shapes. The cancer VII 606 is characterized by a single line quantity style element 402. The cancer VII 606 is characterized by a single line quantity style element 402. The cancer VII 606 is further characterized by a line style element 404 having a dashed line segment. The cancer VII 606 is further characterized by endmark shapes 406 that are parenthetical. The pancreatic VII 606 is further characterized by endmark style element 406 of curved shapes. The pancreatic cancer VII 608 is characterized by a single line quantity style element 402, and the single line segment spans two words. The pancreatic cancer VII 608 is further characterized by a line style element 404 having a solid line segment. The pancreatic cancer VII 608 is further characterized by endmark shapes 406 that are square. The pancreatic cancer VII 608 is further characterized by endmark style element 406 of outlined shapes.

Regarding the flowcharts and block diagrams, the flowchart and block diagrams in the Figures of the present disclosure illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
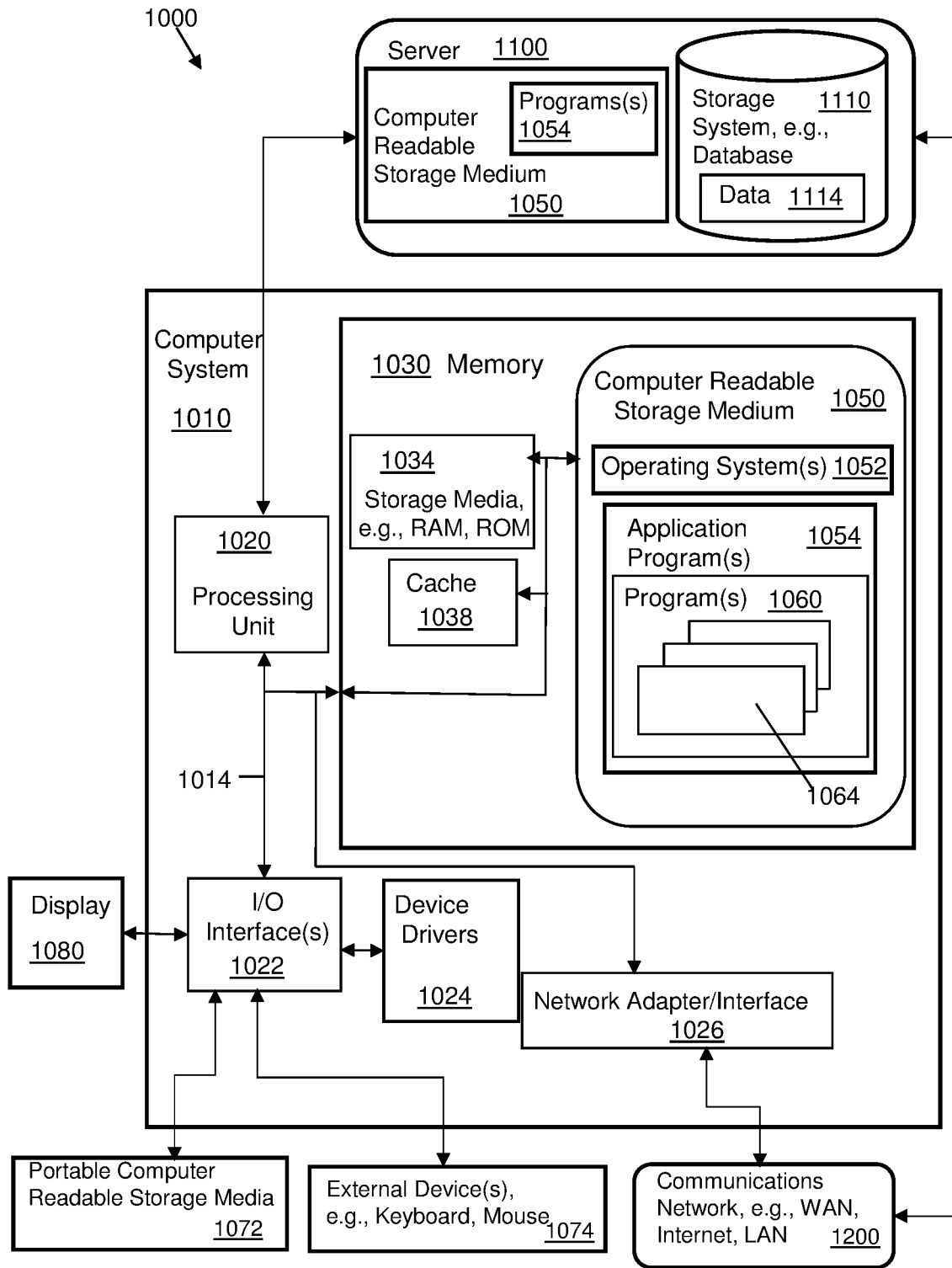
FIG. 7 is a schematic block diagram depicting a computer system according to an embodiment of the disclosure which may be incorporated, all or in part, in one or more computers or devices shown in FIG. 1, and cooperates with the systems and methods shown in FIG. 1.

Referring to FIG. 7, a system or computer environment 1000 includes a computer diagram 1010 shown in the form of a generic computing device. The method 100, for example, may be embodied in a program 1060, including program instructions, embodied on a computer readable storage device, or computer readable storage medium, for example, generally referred to as memory 1030 and more specifically, computer readable storage medium 1050. Such memory and/or computer readable storage media includes non-volatile memory or non-volatile storage. For example, memory 1030 can include storage media 1034 such as RAM (Random Access Memory) or ROM (Read Only Memory), and cache memory 1038. The program 1060 is executable by the processor 1020 of the computer system 1010 (to execute program steps, code, or program code). Additional data storage may also be embodied as a database 1110 which includes data 1114. The computer system 1010 and the program 1060 are generic representations of a computer and program that may be local to a user, or provided as a remote service (for example, as a cloud based service), and may be provided in further examples, using a website accessible using the communications network 1200 (e.g., interacting with a network, the Internet, or cloud services). It is understood that the computer system 1010 also generically represents herein a computer device or a computer included in a device, such as a laptop or desktop computer, etc., or one or more servers, alone or as part of a datacenter. The computer system can include a network adapter/interface 1026, and an input/output (I/O) interface(s) 1022. The I/O interface 1022 allows for input and output of data with an external device 1074 that may be connected to the computer system. The network adapter/interface 1026 may provide communications between the computer system a network generically shown as the communications network 1200.

The computer 1010 may be described in the general context of computer system-executable instructions, such as program modules, being executed by a computer system. Generally, program modules may include routines, programs, objects, components, logic, data structures, and so on that perform particular tasks or implement particular abstract data types. The method steps and system components and techniques may be embodied in modules of the program 1060 for performing the tasks of each of the steps of the method and system. The modules are generically represented in the figure as program modules 1064. The program 1060 and program modules 1064 can execute specific steps, routines, sub-routines, instructions or code, of the program.

The method of the present disclosure can be run locally on a device such as a mobile device, or can be run a service, for instance, on the server 1100 which may be remote and can be accessed using the communications network 1200. The program or executable instructions may also be offered as a service by a provider. The computer 1010 may be practiced in a distributed cloud computing environment where tasks are performed by remote processing devices that are linked through a communications network 1200. In a distributed cloud computing environment, program modules may be located in both local and remote computer system storage media including memory storage devices.

The computer 1010 can include a variety of computer readable media. Such media may be any available media that is accessible by the computer 1010 (e.g., computer system, or server), and can include both volatile and non-volatile media, as well as, removable and non-removable media. Computer memory 1030 can include additional computer readable media in the form of volatile memory, such as random access memory (RAM) 1034, and/or cache memory 1038. The computer 1010 may further include other removable/non-removable, volatile/non-volatile computer storage media, in one example, portable computer readable storage media 1072. In one embodiment, the computer readable storage medium 1050 can be provided for reading from and writing to a non-removable, non-volatile magnetic media. The computer readable storage medium 1050 can be embodied, for example, as a hard drive. Additional memory and data storage can be provided, for example, as the storage system 1110 (e.g., a database) for storing data 1114 and communicating with the processing unit 1020. The database can be stored on or be part of a server 1100. Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1014 by one or more data media interfaces. As will be further depicted and described below, memory 1030 may include at least one program product which can include one or more program modules that are configured to carry out the functions of embodiments of the present invention.

The method(s) described in the present disclosure, for example, may be embodied in one or more computer programs, generically referred to as a program 1060 and can be stored in memory 1030 in the computer readable storage medium 1050. The program 1060 can include program modules 1064. The program modules 1064 can generally carry out functions and/or methodologies of embodiments of the invention as described herein. The one or more programs 1060 are stored in memory 1030 and are executable by the processing unit 1020. By way of example, the memory 1030 may store an operating system 1052, one or more application programs 1054, other program modules, and program data on the computer readable storage medium 1050. It is understood that the program 1060, and the operating system 1052 and the application program(s) 1054 stored on the computer readable storage medium 1050 are similarly executable by the processing unit 1020. It is also understood that the application 1054 and program(s) 1060 are shown generically, and can include all of, or be part of, one or more applications and program discussed in the present disclosure, or vice versa, that is, the application 1054 and program 1060 can be all or part of one or more applications or programs which are discussed in the present disclosure. It is also understood that the control system 70 (shown in FIG. 5) can include all or part of the computer system 1010 and its components, and/or the control system can communicate with all or part of the computer system 1010 and its components as a remote computer system, to achieve the control system functions described in the present disclosure. It is also understood that the one or more communication devices 110 shown in FIG. 1 similarly can include all or part of the computer system 1010 and its components, and/or the communication devices can communicate with all or part of the computer system 1010 and its components as a remote computer system, to achieve the computer functions described in the present disclosure.

One or more programs can be stored in one or more computer readable storage media such that a program is embodied and/or encoded in a computer readable storage medium. In one example, the stored program can include program instructions for execution by a processor, or a computer system having a processor, to perform a method or cause the computer system to perform one or more functions.

The computer 1010 may also communicate with one or more external devices 1074 such as a keyboard, a pointing device, a display 1080, etc.; one or more devices that enable a user to interact with the computer 1010; and/or any devices (e.g., network card, modem, etc.) that enables the computer 1010 to communicate with one or more other computing devices. Such communication can occur via the Input/Output (I/O) interfaces 1022. Still yet, the computer 1010 can communicate with one or more networks 1200 such as a local area network (LAN), a general wide area network (WAN), and/or a public network (e.g., the Internet) via network adapter/interface 1026. As depicted, network adapter 1026 communicates with the other components of the computer 1010 via bus 1014. It should be understood that although not shown, other hardware and/or software components could be used in conjunction with the computer 1010. Examples, include, but are not limited to: microcode, device drivers 1024, redundant processing units, external disk drive arrays, RAID systems, tape drives, and data archival storage systems, etc.

It is understood that a computer or a program running on the computer 1010 may communicate with a server, embodied as the server 1100, via one or more communications networks, embodied as the communications network 1200. The communications network 1200 may include transmission media and network links which include, for example, wireless, wired, or optical fiber, and routers, firewalls, switches, and gateway computers. The communications network may include connections, such as wire, wireless communication links, or fiber optic cables. A communications network may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. A network may also include a number of different types of networks, such as, for example, an intranet, a local area network (LAN), or a wide area network (WAN).

In one example, a computer can use a network which may access a website on the Web (World Wide Web) using the Internet. In one embodiment, a computer 1010, including a mobile device, can use a communications system or network 1200 which can include the Internet, or a public switched telephone network (PSTN) for example, a cellular network. The PSTN may include telephone lines, fiber optic cables, transmission links, cellular networks, and communications satellites. The Internet may facilitate numerous searching and texting techniques, for example, using a cell phone or laptop computer to send queries to search engines via text messages (SMS), Multimedia Messaging Service (MMS) (related to SMS), email, or a web browser. The search engine can retrieve search results, that is, links to websites, documents, or other downloadable data that correspond to the query, and similarly, provide the search results to the user via the device as, for example, a web page of search results.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
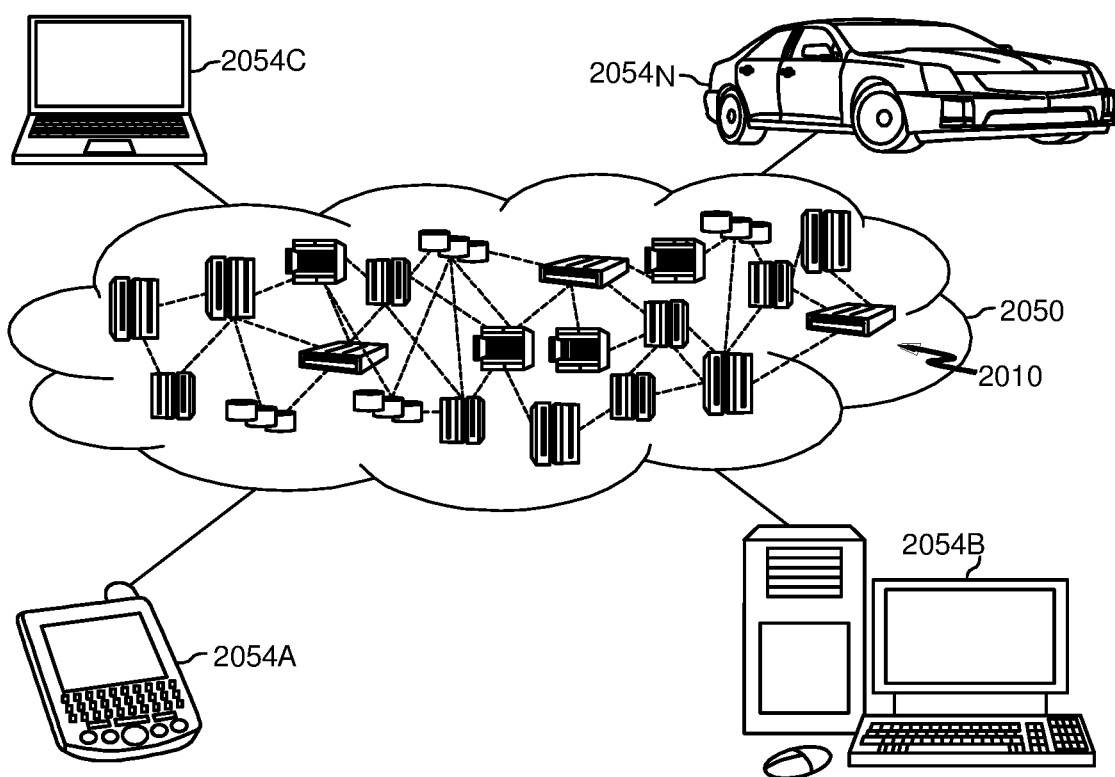
FIG. 8 depicts a cloud computing environment according to an embodiment of the present invention.

Referring now to FIG. 8, illustrative cloud computing environment 2050 is depicted. As shown, cloud computing environment 2050 includes one or more cloud computing nodes 2010 with which local computing devices used by cloud consumers, such as, for example, personal digital assistant (PDA) or cellular telephone 2054A, desktop computer 2054B, laptop computer 2054C, and/or automobile computer system 2054N may communicate. Nodes 2010 may communicate with one another. They may be grouped (not shown) physically or virtually, in one or more networks, such as Private, Community, Public, or Hybrid clouds as described hereinabove, or a combination thereof. This allows cloud computing environment 2050 to offer infrastructure, platforms and/or software as services for which a cloud consumer does not need to maintain resources on a local computing device. It is understood that the types of computing devices 2054A-N shown in FIG. 5 are intended to be illustrative only and that computing nodes 2010 and cloud computing environment 2050 can communicate with any type of computerized device over any type of network and/or network addressable connection (e.g., using a web browser).

Figure 9:
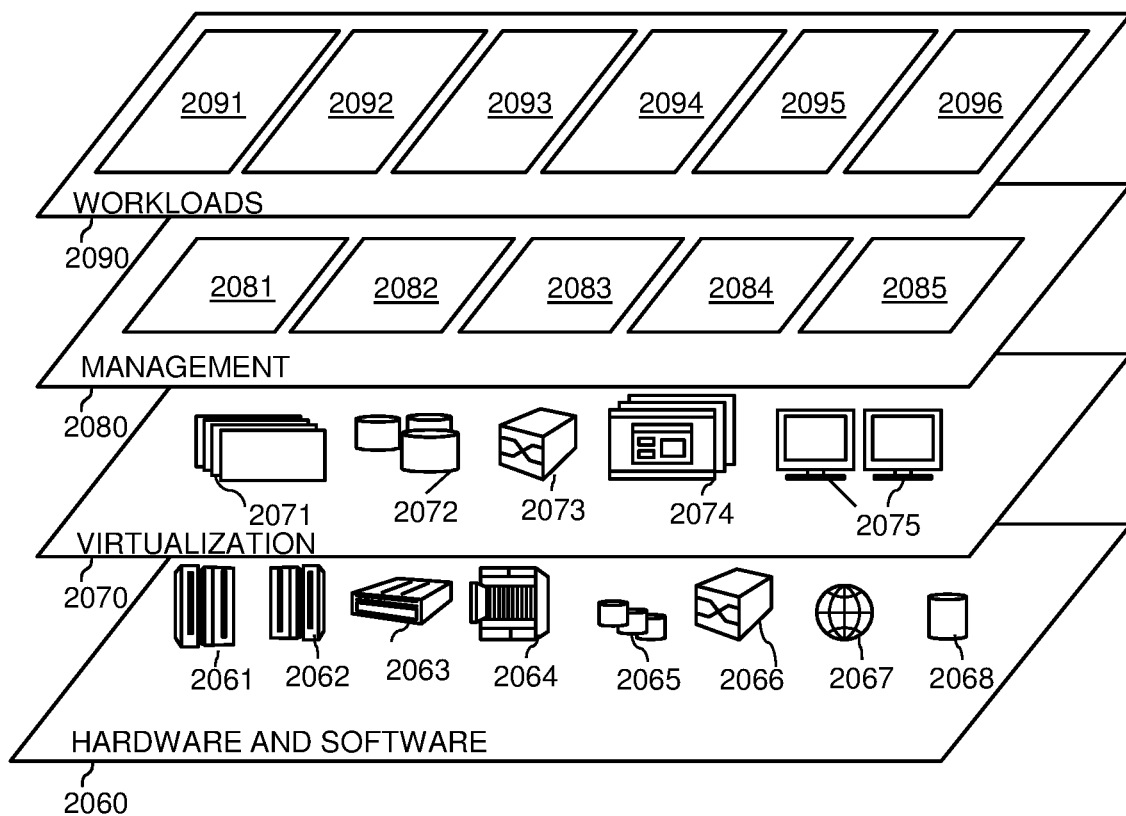
FIG. 9 depicts abstraction model layers according to an embodiment of the present invention.

Referring now to FIG. 9, a set of functional abstraction layers provided by cloud computing environment 2050 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 2060 includes hardware and software components. Examples of hardware components include: mainframes 2061; RISC (Reduced Instruction Set Computer) architecture based servers 2062; servers 2063; blade servers 2064; storage devices 2065; and networks and networking components 2066. In some embodiments, software components include network application server software 2067 and database software 2068.

Virtualization layer 2070 provides an abstraction layer from which the following examples of virtual entities may be provided: virtual servers 2071; virtual storage 2072; virtual networks 2073, including virtual private networks; virtual applications and operating systems 2074; and virtual clients 2075.

In one example, management layer 2080 may provide the functions described below. Resource provisioning 2081 provides dynamic procurement of computing resources and other resources that are utilized to perform tasks within the cloud computing environment. Metering and Pricing 2082 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 2083 provides access to the cloud computing environment for consumers and system administrators. Service level management 2084 provides cloud computing resource allocation and management such that required service levels are met. Service Level Agreement (SLA) planning and fulfillment 2085 provide pre-arrangement for, and procurement of, cloud computing resources for which a future requirement is anticipated in accordance with an SLA.

Workloads layer 2090 provides examples of functionality for which the cloud computing environment may be utilized. Examples of workloads and functions which may be provided from this layer include: mapping and navigation 2091; software development and lifecycle management 2092; virtual classroom education delivery 2093; data analytics processing 2094; transaction processing 2095; and visually representing concepts conveyed in delivered content and relationships among them in a manner that is discernable and visually-accessible. 2096.

The descriptions of the various embodiments of the present invention have been presented for purposes of illustration, but are not intended to be exhaustive or limited to the embodiments disclosed. Likewise, examples of features or functionality of the embodiments of the disclosure described herein, whether used in the description of a particular embodiment, or listed as examples, are not intended to limit the embodiments of the disclosure described herein, or limit the disclosure to the examples described herein. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer implemented method to distinguish relationships among concepts of conveyance contained within delivered content, said process comprising:
   receiving, by said computer, a plurality of concepts of conveyance;
   responsive to receiving said plurality of concepts of conveyance, determining, by said computer, a first visual identification indicia for a first of said plurality of concepts, said first visual identification indicia being characterized by a first combination of appearance style elements selected from a plurality of visual attribute categories, wherein said appearance style elements (ASEs) have sufficient visual contrast relative to one another to represent distinguishable relationships among individual concepts of conveyance, pairs of concepts of conveyance and multiple concepts of conveyance that are overlapping;
   responsive to determining said first visual identification indicia, iteratively determining, by said computer, a corresponding visual identification indicia for each of said remaining plurality of concepts of conveyance, each of said visual identification indicia being characterized by a unique corresponding combination of appearance style elements selected from said plurality of visual attribute categories;
   determining, by the computer, a set of ASEs for a concept of conveyance (COC), and the ASE set includes ASEs identified for strategic reuse;
   recording, by the computer, the set of ASEs for each COC in a reference table to ensure that unique permutations are generated to identify distinct COCs of the plurality COCs by checking the reference table; and
   responsive to determining said visual identification indicia for each concept of conveyance, presenting, by said computer, a visualization of said plurality of concepts of conveyance, said visualization distinguishing relationships among said plurality of concepts of conveyance.

2. The method of claim 1, wherein said appearance style elements are selected, at least in part, in accordance with visual accessibility consideration factors.

3. The method of claim 1, wherein:
   said visual identification indicia are line segments; and
   wherein said appearance style elements are selected from a list consisting of indicia endmarks, indicia line style, indicia line thickness, indicia line quantity, and indicia line color.

4. The method of claim 3, wherein one of said selected appearance style elements includes a first indicia endmark and a second indicia endmark, said first and second endmarks being different.

5. The method of claim 3, wherein said selected appearance style elements include a plurality of line styles.

6. The method of claim 3, wherein one of said selected appearance style elements includes a plurality of line thicknesses.

7. The method of claim 1, wherein said visual identification indicia have at least one attribute in common.

8. The method of claim 1, wherein at least two of said concepts of conveyance share a common characteristic and wherein said visual identification indicia are selected, at least in part, in accordance with said shared characteristic.

9. A system to optimize input component enablement to distinguish relationships among concepts of conveyance contained within delivered content, which comprises:
a computer system comprising a computer readable storage medium having program instructions embodied therewith, the program instructions executable by a computer to cause the computer to:
receive a plurality of concepts of conveyance;
responsive to receiving said plurality of concepts of conveyance, determine a first visual identification indicia for a first of said plurality of concepts of conveyance, said first visual identification indicia being characterized by a first combination of appearance style elements selected from a plurality of visual attribute categories, wherein said appearance style elements have sufficient visual contrast relative to one another to represent distinguishable relationships among individual concepts of conveyance, pairs of concepts of conveyance and multiple concepts of conveyance that are overlapping;
responsive to determining said first visual identification indicia, iteratively determine a corresponding visual identification indicia for each of said remaining plurality of concepts of conveyance, each of said visual identification indicia being characterized by a unique corresponding combination of appearance style elements selected from said plurality of visual attribute categories;
determine, by the computer, a set of ASEs for a concepts of conveyance (COC), and the ASE set includes ASEs identified for strategic reuse;
record, by the computer, the set of ASEs for each COC in a reference table to ensure that unique permutations are generated to identify distinct COCs of the plurality COCs by checking the reference table; and
responsive to determining said visual identification indicia for each concept of conveyance, present a visualization of said plurality of concepts of conveyance, said visualization distinguishing relationships among said plurality of concepts of conveyance.

10. The system of claim 9, wherein said appearance style elements are selected, at least in part, in accordance with visual accessibility consideration factors.

11. The system of claim 9, wherein:
said visual identification indicia are line segments; and
wherein said appearance style elements are selected from a list consisting of indicia endmarks, indicia line style, indicia line thickness, and indicia line color.

12. The system of claim 11, wherein one of said selected appearance style elements includes a first indicia endmark and a second indicia endmark, said first and second endmarks being different.

13. The system of claim 11, wherein said selected appearance style elements include a plurality of line styles.

14. The system of claim 11, wherein one of said selected appearance style elements includes a plurality of line thicknesses.

15. The system of claim 9, wherein said visual identification indicia have at least one attribute in common.

16. The system of claim 9, wherein at least two of said concepts of conveyance of conveyance share a common characteristic and wherein said visual identification indicia are selected, at least in part, in accordance with said shared characteristic.

17. Computer program product to distinguish relationships among concepts of conveyance contained within delivered content, the computer program product comprising a computer readable storage medium having program instructions embodied therewith, the program instructions executable by a computer to cause the computer to:
receive, using said computer, a plurality of concepts of conveyance;
responsive to receiving said plurality of concepts of conveyance, determine, using said computer, a first visual identification indicia for a first of said plurality of concepts of conveyance, said first visual identification indicia being characterized by a first combination of appearance style elements selected from a plurality of visual attribute categories, wherein said appearance style elements have sufficient visual contrast relative to one another to represent distinguishable relationships among individual concepts of conveyance, pairs of concepts of conveyance and multiple concepts of conveyance that are overlapping;
responsive to determining said first visual identification indicia, iteratively determine, using said computer, a corresponding visual identification indicia for each of said remaining plurality of concepts of conveyance, each of said visual identification indicia being characterized by a unique corresponding combination of appearance style elements selected from said plurality of visual attribute categories;
determine, by the computer, a unique set of ASEs for a concepts of conveyance (COC), and the ASE set includes ASEs identified for strategic reuse;
record, by the computer, the set of ASEs for each COC in a reference table to ensure that unique permutations are generated to identify distinct COCs of the plurality COCs by checking the reference table; and
responsive to determining said visual identification indicia for each concept of conveyance, present, using said computer, a visualization of said plurality of concepts of conveyance, said visualization distinguishing relationships among said plurality of concepts of conveyance.

18. The computer program product of claim 17, wherein said appearance style elements are selected, at least in part, in accordance with visual accessibility consideration factors.

19. The computer program product of claim 17, wherein:
said visual identification indicia are line segments; and
wherein said appearance style elements are selected from a list consisting of indicia endmarks, indicia line style, indicia line thickness, and indicia line color.

20. The computer program product of claim 19, wherein one of said selected appearance style elements includes a first indicia endmark and a second indicia endmark, said first and second endmarks being different.

* * * * *